US006946551B2

(12) United States Patent
Long et al.

(10) Patent No.: US 6,946,551 B2
(45) Date of Patent: Sep. 20, 2005

(54) PREPARATION OF HYALURONIC ACID FROM EGGSHELL MEMBRANE

(75) Inventors: Frank Daniel Long, Neosho, MO (US); Randall Gene Adams, Carthage, MO (US); Dale Paul DeVore, Chelmsford, MA (US)

(73) Assignee: New Life Resources, LLC, Carthage, MO (US)

( * ) Notice: Subject to any disclaimer, the term of this patent is extended or adjusted under 35 U.S.C. 154(b) by 0 days.

(21) Appl. No.: 10/616,278

(22) Filed: Jul. 9, 2003

(65) Prior Publication Data

US 2004/0180851 A1 Sep. 16, 2004

Related U.S. Application Data

(60) Provisional application No. 60/453,891, filed on Mar. 12, 2003.

(51) Int. Cl.$^7$ ........................ A61K 31/728; C08B 37/00
(52) U.S. Cl. ...................... 536/55.3; 514/53; 514/54; 536/55.1; 536/55.2
(58) Field of Search .............................. 536/55.1, 55.2, 536/55.3; 514/53, 54

(56) References Cited

U.S. PATENT DOCUMENTS

| | | | |
|---|---|---|---|
| 3,194,732 A | | 7/1965 | Neuhauser |
| 4,141,973 A | * | 2/1979 | Balazs ........................ 514/54 |
| 4,517,295 A | * | 5/1985 | Bracke et al. ............... 435/101 |
| 4,713,448 A | | 12/1987 | Balazs et al. |
| 4,716,224 A | * | 12/1987 | Sakurai et al. ............. 536/55.1 |
| 4,784,990 A | | 11/1988 | Nimrod et al. |
| 4,879,375 A | | 11/1989 | Cullis-Hill |
| 4,992,264 A | | 2/1991 | Diot et al. |
| 5,079,236 A | | 1/1992 | Drizen et al. |
| 5,099,013 A | | 3/1992 | Balazs et al. |
| 5,141,964 A | | 8/1992 | Noel |
| 5,166,331 A | | 11/1992 | Della Valle et al. |
| 5,316,926 A | | 5/1994 | Brown et al. |
| 5,411,874 A | | 5/1995 | Ellwood et al. |
| 5,415,875 A | | 5/1995 | Kakoki et al. |
| 5,460,832 A | | 10/1995 | Yamaguchi et al. |
| 5,538,740 A | | 7/1996 | Abad |
| 5,559,104 A | | 9/1996 | Romeo et al. |
| 5,646,129 A | | 7/1997 | Callegaro et al. |
| 5,783,691 A | | 7/1998 | Malson et al. |
| 5,869,063 A | | 2/1999 | Lezdey et al. |
| 5,925,626 A | | 7/1999 | Della Valle et al. |
| 5,928,659 A | | 7/1999 | Moy |
| 6,030,958 A | | 2/2000 | Burns et al. |
| 6,090,596 A | | 7/2000 | Stahl |
| 6,194,392 B1 | | 2/2001 | Falk et al. |
| 6,217,913 B1 | | 4/2001 | Mohammadi |
| 6,218,373 B1 | | 4/2001 | Falk et al. |
| 6,255,295 B1 | * | 7/2001 | Henderson et al. ........... 514/54 |
| 6,337,389 B1 | | 1/2002 | Wolfinbarger, Jr. |
| 6,399,083 B1 | | 6/2002 | Pillai et al. |
| 6,498,204 B1 | | 12/2002 | Ubara |

| | | |
|---|---|---|
| 2002/0037312 A1 | 3/2002 | Brown et al. |
| 2003/0175332 A1 | 9/2003 | Brown et al. |

FOREIGN PATENT DOCUMENTS

JP          1043502         2/1989

OTHER PUBLICATIONS

Osuoji, C.J. "Acid Glycosaminoglycan of Eggshell Membrane", Biochimica et Biophysica Acta, 1971, 244, 481–483.*

Baker, J.R. et al, "A Study of the Organic Material od Hen's–Egg Shell", Biochemical Journal, 1962, 82, 352–361.*

Baker, J.R. et al., "A Study of the Organic Material of Hen's–Egg Shell", *Biochemical Journal*, 1962, 82, 352–361.

"Egg Science and Technology", Eds. W.J. Stadelman and O.J. Cotterill, Food Products Press, a subsidiary of The Haworth Press, Bingham, NY, 1990.

Britton, W.M. and Hale, K.K., "Amino Acid Analysis of Shell Membranes of Eggs from Young and Old Hens Varying in Shell Quality", *Poultry Science*, 56:865–871, 1977.

Cifonelli, J.A., "The Colormetric Estimation of Uronic Acid", *Methodology of Connective Tissue Research*, ED:DA Hall, Joynson–Bruvvers Ltd., Oxford, 1976, Chapter 26, pp. 253–256.

Armstrong, DC and Johns, MR, "Improved Molecular Weight Analysis of Streptococcal Hyaluronic Acid by Size Exclusion Chromatography" in Biotechnology Techniques.

Fernandez, M.S., Araya, M., and Arias, JL, "Eggshells are Shaped by a Precise Spatio–Temporal Arrangement of Sequentially Deposited Macromolecules", *Matrix. Biol.*, 16:13–20, 1997.

Takahashi, K., Shirai, K., Kitamura, M., Hattori, M., "Soluble Egg Shell Membrane Protein as a Regulating Material for Collagen Matrix Reconstruction", *Biosci. Biotechnology & Biochemistry*, 60:1299–1302, 1996.

T.C. Laurent, "Structure of Hyaluronic Acid", *Chem. and Mol. Biol. of Intracellular Matrix*, vol. 2, 1970, pp. 703–732.

O.H. Lowry et al., "Protein Measurement with the Folin Phenol Reagent", *The Journal of Biological Chemistry*, vol. 193 (1951) pp. 265–275.

(Continued)

*Primary Examiner*—James O. Wilson
*Assistant Examiner*—Ganapathy Krishnan
(74) *Attorney, Agent, or Firm*—Hoffmann & Baron, LLP

(57) ABSTRACT

Compositions and methods of preparing compositions containing hyaluronic acid derived from eggshell membrane are disclosed. The compositions can contain essentially pure hyaluronic acid or hyaluronic acid in combination with other naturally occurring constituents derived from eggshell membrane. In another aspect, the invention is directed to a method of treating a mammal that will benefit from the administration of hyaluronic acid, which includes administering to the mammal a composition containing hyaluronic acid derived from eggshell membrane.

29 Claims, No Drawings

OTHER PUBLICATIONS

W.D. Comper et al., "Physiological Function of Connective Tissue Polysaccharides" *Physiological Reviews*, vol. 58, No. 1 (1978) pp. 255–315.

K. Meyer, "Chemical Structure of Hyaluronic Acid", *Fed. Proceed*, vol. 17 (1958) pp. 1075–1077.

E.A. Balazs et al., "Hyaluronic Acid and Replacement of Vitreous and Aqueous Humor" *Mod. Probl. Ophthal.*, vol. 10 (1972) pp. 3–21.

U.B.G. Laurent, "Hyaluronate in Human Aqueous Humor", *Arch Ophtalmol.*, vol. 101 (1983) pp. 129–130., vol. 101 (1983) pp. 129–130.

Nakano T., Ikawa NI, Ozimek., "Chemical composition of chicken eggshell and shell membranes,"*Poult Sci.* 2003, 82(3):510–4 [Abstract].

Dupoirieux L., Pourquier D., Picot MC, Neves M., "Comparative study of three different membranes for guided bone regeneration of rat cranial defects," *Int J Oral Maxillofac Surg* 2001, 30(1):58–62 [Abstract].

Dupoirieux L., Neves M., Pourquier D., "Comparison of pericranium and eggshell as space fillers used in combination with guided bone regeneration: an experimental study," *J Oral Maxillofac Surg* 2000, 58(1):40–6 [Abstract].

Arias JL, Nakamura O, Fernandez MS, Wu JJ, Knigge P, Eyre DR, Caplan Al, "Role of type X collagen on experimental mineralization of eggshell membranes," *Connect Tissue Res* 1997, 36(1):21–33.

Arias JL, Fernandez MS, Dennis JE, Caplan Al, "Collagens of the chicken eggshell membrane," *Connect Tissue Res* 1991, 26(1–2):37–45 [Abstract].

Starcher BC, King GS, "The presence of desmosine and isodesmosine in eggshell membrane protein," *Connect Tissue Res* 1980, 8(1):53–5 [Abstract].

Osuoji CI, "Acid glycosaminoglycan of eggshell membranes," *Biochim Biophys Acta* 1971, 244(2):481–3.

Gautron J, Hincke MT, Panheleux M, Garcia–Ruiz JM, Boldicke T, Nys Y, "Ovotransferrin is a matrix protein of the hen eggshell membranes and basal calcified layer," *Connect Tissue Res* 2001, 42(4):255–67 [Abstract].

Akagawa M, Wako Y, Suyama K, "Lysyl oxidase coupled with catalase in egg shell membrane," *Biochim Biophys Acta* 1999, 1434(1):151–60 [Abstract].

Suyama K, Fukazawa Y, Umetsu Y, "A new biomaterial, hen egg shell membrane, to eliminate heavy metal ion from their dilute waste solution," *Appl Biochem Biotechnol* 1994, 45–46:871–9[Abstract].

Arias JL, Fernandez MS, Dennis JE, Caplan AL, "The fabrication and collagenous substructure of the eggshell membrane in the isthmus of the hen oviduct," *Matrix* 1991, 11(5);313–20[Abstract].

U.S. Department of Agriculture, Avian Physiology Laboratory, Beltsville, Maryland 20705, "Levels of calcium and soluble collagen in turkey egg shell membranes," *Comp Biochem Physiol A* 1988, 90(3):421–4[Abstract].

Leach RM Jr, Rucker RB, Van Dyke GP, "Egg shell membrane protein: a nonelastin desmosine/isodesmosine–containing protein," *Arch Biochem Biophys* 1981, 207(2):353–9 [Abstract].

Crombie G, Snider R, Faris B, Franzblau C, "Lysine–derived cross–links in the egg shell membrane," *Biochem Biophys Acta* 1981, 640(1):365–7[Abstract].

Harris ED, Blount JE, Leach RM Jr., "Localization of lysyl oxidase in hen oviduct: implications in egg shell membrane formation and composition," *Science* 1980, 208(4439):55–6 [Abstract].

Stevenson IL, "The removal of egg shell membranes by enzyme treatment to facilitate the study of shell microstructure," *Poult Sci* 1980, 59(8):1959–60[Abstract].

Picard J, Paul–Gardais A, Vedel M., "[Sulfated glycoproteins from egg shell membranes and hen oviduct. Isolation and characterization of sulfated glycopeptides (author's transl)]," *Biochim Biophys Acta* 1973, 320(2):427–41 [Abstract].

Robinson DS, King NR, "Mucopolysaccharides of an avian egg shell membrane," *JR Microsc Soc* 1968, 88(1):13–22 [Abstract].

Powrie William, Nakai S., "The Chemistry of eggs and egg products," *Egg Science and Technology* 1990, 97–139.

Wu Tzong–Ming, Rodriguez Juan Pablo, Fink David, Carrino David, Blackwell John, Caplan Arnold, Heuer Arthur, "Crystallization Studies on Avian Eggshell Membranes: Implications for the Molecular Factors Controlling Eggshell Formation," *Matrix Biology* 1995, 14:507–513.

Hall David, "The Colorimetric Estimation of Uronic Acid," *The Methodology of Connective Tissue Research* 1976, 253–256.

Wong Mitchell, Hendrix Mary J.C., Mark Klaus von der, Little Charles, Stern Robert, "Collagen in the Egg Shell Membrane of the Hen," *Developmental Biology* 1984 104:8–36.

Gautron, Bain M., Solomon S, NYS Y., "Soluble matrix of hen's eggshell extracts changes in vitro the rate of calcium carbonate precipitation and crystal morphology," *British Poultry Science* 1996 37, 853–866.

Tomihata Kenji, Ikada Yoshito, "Crosslinking of hyaluronic acid with water–soluble carbodiimide," *J Biomed Mater Res*, 1997, 37, 243–251.

Carrino David, Dennis James, Wu Tzong–Ming, Arias Jose, Fernandez Maria, Rodriguez Juan, Fink David, Heuer Arthur, Caplan Arnold, "The Avian Eggshell Extracellular Matrix as a Model for Biomineralization," *Connective Tissue Research*, 1996, 35(1–4), 325–329.

Hincke M.T., Tsang C.P.W., Courtney M, Hill V, Narbaitz R., "Purification and Immunochemistry of a Soluble Matrix Protein of the Chicken Eggshell," *Calcif Tissue Int*, 1995, 56:578–583.

\* cited by examiner

PREPARATION OF HYALURONIC ACID FROM EGGSHELL MEMBRANE

This application claims the benefit of U.S. Provisional Application No. 60/453,891, filed Mar. 12, 2003, which is incorporated herein by reference in its entirety.

FIELD OF THE INVENTION

The present invention relates to extraction, isolation and purification of hyaluronic acid from eggshell membrane. The hyaluronic acid material from the eggshell membrane contains polydisperse hyaluronic acid for use in various applications.

BACKGROUND

Hyaluronic acid was discovered by Meyer and Palmer in 1934. Karl Meyer isolated the polysaccharide from the vitreous humor. Since it contained uronic acid, Meyer named the substance hyaluronic acid from hyalos (meaning glassy, vitreous) and uronic acid. At physiological pH all carboxyl groups on the uronic acid residue are dissociated and the polysaccharide was named sodium hyaluronate when sodium is the counter ion. In 1986, Balazs suggested the name hyaluranon. This is currently the accepted terminology. The abbreviation "HA" will be used in this application to designate hyaluranon, which includes hyaluronic acid and its metallic salts.

HA is a linear polysaccharide (long-chain biological polymer) formed by repeating disaccharide units consisting of D-glucuronic acid and N-acetyl-D-glucosamine linked by $\beta(1-3)$ and $\beta(1-4)$ glycosidic linkages. HA is distinguished from the other glycosaminoglycans, as it is free from covalent links to protein and sulphuric groups. It is however an integral component of complex proteoglycans. HA is an important component of the intercellular matrix, the material filling the space between the cells of such diverse tissues as skin, tendons, muscles and cartilage.

HA has been discovered as a coat attached to cell surface, as part of large molecular structures, and as free polysaccharide, e.g., in synovial fluid and in the vitreous body. HA is ubiquitous in animals, with the highest concentration found in soft connective tissue. It plays an important role for both mechanical and transport purposes in the body; e.g., it gives elasticity to the joints and rigidity to the vertebrate disks, and it is also a constituent of major importance in the vitreous body of the eye.

HA, because of its high degree of hydration, is probably responsible for the high content of water of some tissues, increasing the resistance of such tissues to compression. This is a role based on hyaluronic acid's capacity to hold more water than any other natural or synthetic polymer. The size (MW) of individual molecules and the potential for intermolecular interactions determines whether a particular HA preparation will form an elastoviscous matrix under given conditions.

The large molecular volume forces the overlap of individual HA molecular domains, resulting in extensive chain entanglement and chain-chain interaction. It is the resulting intertwined polymeric network, which acts as the jelly-like milieu supporting and influencing tissue functions.

Hyaluronic acid serves as a thickening agent to synovial fluid, and the viscoelastic effect is such that under impact a hyaluronic acid solution is hard elastic, but under slow movement the viscosity effect is more operable. The shock absorber effect is particularly important and effective in young people.

HA is a natural lubricant and synovial fluid requires the presence of hyaluronic acid to be an effective lubricant of the synovial membrane. The network-making property plays a primary role in the connective tissue; this role differs from those of the chondroitin sulphate, dermatan sulphate and keratan sulphate, their water retention abilities and, therefore, their solution viscosity being inferior.

Hyaluronic acid may also play an important role in the control of intercellular and interstitial permeability. This theory is supported by the fact that the depolymerization of hyaluronic acid, which occurs in certain pathological conditions of connective tissues, results in an increased permeability of the connective tissue barrier.

Hyaluronic acid is involved in ossification processes. Calcium (II) ions can become strongly associated with a hyaluronic acid proteoglycan and are not readily displaced, even by high concentrations of univalent ions. There is evidence for a role of proteoglycans in regulation of mineral phase separation in calcifying cartilage and calcification itself.

The intraarticular injection of viscoelastic high molecular weight (HMW)-HA solutions provides protection, lubrication, pain reduction and hydration to the articular cartilage and capsular tissues. This injection may restore the damaged HA layer on the articular cartilage surface, bringing about an alleviation of arthritic condition and arrest of the process of disease.

The HA properties are dependent on the molecular weight, the solution concentration, and physiological pH. In low concentrations, the individual chains entangle and form a continuous network in solution, which gives the system interesting properties, such as pronounced viscoelasticity and pseudoplasticity that is unique for a water-soluble polymer at low concentration.

HA exhibits viscous flow, elastic and pseudoplastic properties. This property is unique to HA. Other glycosaminoglycans, GAGs, may form viscous solutions, but only at considerably greater concentrations than HA, and they never form a viscoelastic polymer network. HA has been demonstrated to be important in different activities such as tissue hydration, lubrication, solute transportation, cell migration, cell function, cell differentiation, and cell proliferation.

Sources and Manufacturing of HA: During the 1930s and 1940s Meyer and others isolated hyaluranon from a number of sources and relatively large amounts were found in vitreous, synovial fluid, umbilical cord, skin, and rooster comb. HA has historically been isolated from synovial fluid, umbilical cord, skin, and rooster comb. However, Kendall in 1937 isolated HA from certain strains of bacteria, such as streptococci. Today HA is also obtained from bacterial fermentation.

The isolation of HA from rooster combs typically includes the following steps: An enzymatic digestion, a specific separation in order to remove protein and a purification to provide a crude extract. Further purification steps include precipitation in ethanol and redissolution in sodium chloride solution. Thus, a typical process for isolating HA from rooster comb includes removal of epithelium from the combs, grinding of combs, treatments in acetone and multiple treatments with ethanol and sodium chloride solutions. Several U.S. patents describe methods to isolate and purify hyaluronic acid including U.S. Pat. Nos. 4,141,973; 4,784,990; 5,099,013; 5,166,331; 5,316,926; 5,411,874; 5,559,104 and 5,925,626, which are incorporated herein by reference.

There are some differences between the isolation-origin and the fermentation-origin HA. The HA obtained from isolation methods has the natural structure of the glycosaminoglycan (formally called mucopolysaccharide) in natural tissues. In this sense it is much more porous than that obtained by fermentation, and therefore can exhibit great differences of dispersability in water. HA obtained by bacterial fermentation typically includes higher levels of bacteria and, when cultured, has a higher number of colony forming units (c.f.u.) than HA obtained by isolation methods, due to the high level of nutrients in the fermentation media. Further, fermentation-origin HA typically includes significant levels of endotoxins that must be removed. The HA obtained by fermentation also needs to be more purified in order to eliminate as many bacterial proteins as possible.

There are also drawbacks with HA prepared by many of the known methods or from known sources. These drawbacks can include, for example, an inflammatory response when used in compositions for treating mammals and post-operative complications in ocular surgery. Although, many of the drawbacks can be avoided or minimized by additional processing, it results in an increased costs in obtaining HA having the requisite purity and functionality.

Although HA obtained from known sources, discussed above, have found use in connection with humans and animals, e.g., as ingredients for cosmetics, pharmaceuticals and nutraceuticals, these known sources contain relatively low levels of HA or require significant processing to produce HA in the required purity. This also results in a relatively high cost for useable HA.

The composition of egg and/or eggshell membranes, as well as the eggshell, have also been previously reported. Eggshell membranes are composed of protein fibers between the albumin and the inner surface of the shell. The proteins have a high concentration of arginine, glutamic acid, methionine, histidine, cystine, and proline.[1] Additional investigations of eggshell membrane have demonstrated the presence of high concentrations of collagen, including Type I and Type X collagen.[2,3] Further investigations have identified keratan and dermatan sulfate in eggshell.[4] Studies have also reported the absence of uronic acid in eggshell membrane.[5] One study, which investigated the acid glycosaminoglycan content of the isthmus region of hen oviduct and the egg membrane of shell-free eggs, reported very low levels of hyaluronic acid in the egg membrane collected from the shell-free eggs.[6] However, neither the presence of significant quantities of hyaluronic acid (HA) in eggshell membrane nor the extraction of HA from eggshell membrane have been previously reported.

Thus, there is a need for new sources of HA, which have higher concentrations of the naturally occurring HA. There is also a need for HA derived from new sources, which does not have the problems associated with known sources of HA, requires less processing and/or results in more cost effective methods for obtaining useful HA products.

SUMMARY OF THE INVENTION

The present invention is based on the discovery, for the first time, of the presence of significant quantities of HA in eggshell membrane. This invention includes extraction, isolation and purification of hyaluronic acid material from a novel source, eggshell membrane, and preparation of useful isolate(s) and compositions based on the discovery.

The inventors have investigated eggshell membrane, which was cleanly separated from egg and eggshell, by analyzing for amino acid profiles, glucosamine, chondroitin, and HA. HA content was measured using three different assays as follows: (1) colorimetric measurement for uronic acid using a modified carbazole reaction[7]—uronic acid composes about 50% of the HA molecule. (2) Assay using an ELISA test prepared by Corgenix, Inc.—this enzyme-linked binding protein assay uses a capture molecule known as hyaluronic acid binding protein (HABP) to measure HA concentration. (3) Measurement by size exclusion chromatography using the method of Armstrong and Johns.[8]

The first assay method (discussed above) was used to measure HA in aqueous extracts of crude eggshell membranes and in enzyme hydrolysates of eggshell membranes. Results indicated HA concentrations ranging from 0.1% to more than 2% in tested samples. It is suspected that these uronic acid concentrations are lower than expected due to interference of the calorimetric reactions by protein contaminants. More sensitive and specific ELISA assays indicated significantly higher levels of HA in eggshell membrane samples. Concentrations ranged from 5% to more than 10% on a wet weight basis. Measurement using size exclusion chromatography confirmed the presence of HA.

It is believed that these findings are the first reporting of significant quantities of HA, glucosamine and chondroitin in eggshell membrane. Concentrations of glucosamine and chondroitin were 10% and 9% of wet membrane weight, respectively. Furthermore, the concentrations of HA in eggshell membrane appear to be higher than those reported for any other tissue, including cocks comb.

After confirming the presence of significant amounts of HA in eggshell membranes, HA was extracted and purified from crude eggshell membrane using techniques for extracting HA from other source materials. The molecular weight of purified HA was measured using HPLC techniques. Results indicated a relatively low molecular weight HA, between 50,000 and 100,000 daltons. The inventors believe this is the first report of significant quantities of HA in eggshell membrane and that eggshell membrane may be an abundant source of HA for a variety of applications.

Thus, in one aspect, the present invention is a hyaluronic acid isolate which includes HA derived from eggshell membrane. The eggshell membrane preferably contains at least about 0.5 wt %, more preferably at least about 1 wt %, and most preferably from about 1 to about 5 wt % hyaluronic acid. The hyaluronic acid isolate preferably contains at least about 80 wt %, more preferably at least about 90 wt %, and most preferably at least about 95 wt % hyaluronic acid.

The hyaluronic acid isolate can be derived from the eggshell membrane by extracting a hyaluronic acid fraction from the eggshell membrane. In one embodiment, the hyaluronic acid fraction is purified to provide the hyaluronic acid isolate having a desired naturally occurring HA content and can be purified to provide a cosmetic grade and/or pharmaceutical grade hyaluronic acid.

The hyaluronic acid isolate can also include other naturally occurring material derived from eggshell membrane selected from the group consisting of a hexosamine, chondroitin sulfate and combinations thereof. The hexosamine can be selected from the group consisting of N-acetyl-D-glucosamine, N-acetyl-D-galactosamine, hexoses and mixtures thereof. In this embodiment, a composition can be prepared in which therapeutically effective amounts of the hexosamine and/or chondroitin sulfate are present.

The hexosamine, e.g., glucosamine, is preferably present in an amount of at least about 0.05, more preferably in the range of about 0.5 to about 10, and most preferably in the range of about 0.5 to about 5 wt %.

The chondroitin sulfate is preferably present in an amount of at least about 0.05, more preferably in the range of about 0.5 to about 10, and most preferably in the range of about 0.5 to about 5 wt %.

In another aspect, the invention is directed to a method for producing a hyaluronic acid composition which includes extracting a hyaluronic acid composition from eggshell membrane. The method preferably includes the step of separating the eggshell membrane from the egg yolk, egg white and eggshell prior to the extracting step.

The hyaluronic acid composition preferably contains at least about 80 wt %, at least about 90 wt %, and most preferably at least about 95 wt % hyaluronic acid.

In one embodiment, the hyaluronic acid composition is substantially pure hyaluronic acid. The hyaluronic acid composition preferably contains a naturally occurring hyaluronic acid having an average molecular weight of less than about 1,000,000, more preferably in the range of from about 50,000 to about 500,000, and most preferably in the range from about 50,000 to about 250,000 daltons. The molecular weight can be increased by additional processing, e.g., by cross-linking the hyaluronic acid. There are numerous methods to crosslink hyaluronic acid. Selected patent references describing crosslinking methods include U.S. Pat. No. 4,716,224 (polyfunctional epoxy compounds); U.S. Pat. No. 5,099,013 (formaldehyde); U.S. Pat. No. 5,783,691 (phosphorus acid halides); and U.S. Pat. No. 6,030,958 (water soluble carbodiimides). In addition, selected literature citations include Luo, et. al.[9], Bulpitt, et al.[10], Prestwich et al.[11], and Tomihata, et al.[12]

In one embodiment, the hyaluronic acid composition can also include a naturally occurring material derived from eggshell membrane selected from the group consisting of a hexosamine, chondroitin sulfate and combinations thereof, as discussed more fully above with respect to the hyaluronic acid isolate.

In yet another aspect, the invention is directed to a composition for use with mammals, including both humans and animals. The composition includes hyaluronic acid derived from eggshell membrane. The composition can also include other naturally occurring constituents derived from eggshell membrane which are useful to humans or animals. These other constituents can include glucosamine and/or chondroitin sulfate.

Preferred uses of the composition include use as a lubricant or moisturizing agent in cosmetics or eye drops, an orally administered nutraceutical or a locally administered treatment for joints afflicted with osteoarthritis.

Thus, in another aspect, the invention is directed to a method of treating a mammal having a condition which will benefit from the administration of HA, which includes administering a composition rich in HA derived from eggshell membrane.

In yet another aspect, the invention is directed to a method for producing a product for use with mammals which includes extracting a hyaluronic acid composition from eggshell membrane and incorporating the hyaluronic acid composition in a product for use with mammals. Preferably, the eggshell membrane is first separated from the egg white, egg yolk and eggshell prior to extracting the hyaluronic acid composition. The hyaluronic acid composition can also be purified prior to incorporation into the product for use with mammals.

As a result of the present invention, an extremely useful, high grade HA can be provided, alone or along with other naturally-occurring beneficial components, which can be used in compositions and treatments for mammals, i.e., animals and humans.

DETAILED DESCRIPTION

The present invention reports the presence of high concentrations of HA in eggshell membrane and describes extraction, purification, and analysis of HA derived from eggshell membrane.

The composition of eggshell membranes was analyzed from a source of cracked eggs, which included the eggshells with the membrane attached. The eggshell membranes were first separated from the eggshells. Following separation from the shell, the eggshell membrane was tested for amino acid profile and for glucosamine, hyaluronic acid, and chondroitin. Initial results from the Corgenix ELISA assay showed HA concentrations from 5%–10% (50 mg/mL to 100 mg/mL). Samples of crude eggshell membrane were processed to extract and purify HA. Initial results demonstrated that the isolated HA exhibited a relatively low concentration of low molecular weight HA (approximately 50,000–100,000 daltons) using size exclusion chromatography and a refractive index detector. Samples of enzyme hydrolyzed eggshell membrane were tested for HA by the uronic acid assay. Results showed HA concentrations between 0.1% and 2% of the total hydrolysate. This hydrolysate represented enzyme treated eggshell membrane diluted about 1:5 in enzyme solution. Therefore, the total HA content of eggshell membrane was between 0.5%–10% HA. This appears to be the highest level of HA measured in any tissue.

The following Table compares the concentration of HA in eggshell membrane to the concentration of HA in other tissues. (from Laurent, T C, Chemistry & Biology of Extracellular Matrix, Academic Press, Volume 2, Pp 763, 1970).

| Source | HA concentration (percent by wet weight) HA content |
|---|---|
| Vitreous Humor | 0.002% |
| Adult Skin | 0.03–0.09% |
| Synovial Fluid | 0.14–0.36% |
| Umbilical Cord | 0.3% |
| Rooster Comb | 0.75% |
| Eggshell Membrane | 0.5–10% by uronic acid analysis |

The inventors believe that eggshell membrane is a valuable source for HA. This HA can be used in various applications including cosmetics, eye drops, nutraceuticals, and various other medical applications. Furthermore, the presence of glucosamine and chondroitin in eggshell membrane suggests the potential application of processed eggshell membrane as a nutraceutical to treat joint pain.

The residue following HA extraction has also been analyzed for hydroxyproline content. Results showed that the wet residue contained 4.5% hydroxyproline. Collagen is composed of about 13% hydroxyproline. Therefore, the total collagen content of the residue is about 35% of the wet weight. This collagen residue may also have important medical and non-medical applications. It is known that eggshell membrane primarily contains Type I collagen. It also contains significant quantities of Type X collagen. Type X collagen may have application in reducing or preventing tissue mineralization.

Therefore, in addition to preparing compositions/products containing substantially pure HA derived from eggshell membrane, the present invention also contemplates useful products derived from eggshell membrane, which include combinations of naturally occurring components from the membrane, such as combinations of the other useful components discussed above.

In one aspect, the present invention is a hyaluronic acid isolate which includes HA derived from eggshell membrane. The eggshell membrane preferably contains at least about 0.5 wt %, more preferably at least about 1 wt %, and most preferably from about 1 to about 5 wt % hyaluronic acid.

The terminology "isolate" as used herein means a product or composition which is set apart from other constituents of eggshell membrane. The hyaluronic acid isolate preferably contains at least about 80 wt %, more preferably at least about 90 wt %, and most preferably at least about 95 wt % hyaluronic acid.

The hyaluronic acid isolate can be derived from the eggshell membrane by extracting a hyaluronic acid fraction from the eggshell membrane. In one embodiment, the hyaluronic acid fraction is purified to provide the hyaluronic acid isolate having a desired naturally occurring HA content. In one embodiment, the hyaluronic acid fraction can be purified to provide a cosmetic grade or a pharmaceutical grade hyaluronic acid.

The hyaluronic acid isolate can also include other naturally occurring materials derived from eggshell membrane. These materials can be selected from the group consisting of a hexosamine, chondroitin sulfate and combinations thereof. The hexosamine can be selected from the group consisting of N-acetyl-D-glucosamine, N-acetyl-D-galactosamine, hexoses and mixtures thereof. In this embodiment, the hyaluronic acid isolate preferably includes therapeutically effective amounts of the hexosamine (e.g., glucosamine), chondroitin sulfate or their combination.

The hexosamine is preferably present in an amount of at least about 0.05, more preferably in the range of about 0.5 to about 10, and most preferably in the range of about 0.5 to about 5 wt %.

The chondroitin sulfate is preferably present in an amount of at least about 0.05, more preferably in the range of about 0.5 to about 10, and most preferably in the range of about 0.5 to about 5 wt %.

The hyaluronic acid isolate is preferably free of any animal body components or trace thereof, e.g., animal tissue, blood or body fluid components, which are detrimental or undesirable for the contemplated use of the HA isolate. The hyaluronic acid isolate is, for example, free of animal body components which can cause an inflammatory response, e.g., certain proteins. The hyaluronic acid isolate is also preferably free of any by-products associated with HA derived from bacterial fermentation, which are detrimental or undesirable for the contemplated use of the HA isolate.

In another aspect, the invention is directed to a method for producing a hyaluronic acid composition which includes extracting a hyaluronic acid composition from eggshell membrane. The method preferably includes the step of separating the eggshell membrane from the egg yolk, egg white and eggshell prior to the extracting step.

Typically, the source of eggshell membrane will be from cracked eggs, where the eggshell membrane is still attached to the eggshell. The eggshell membrane can be separated from the eggshell in any convenient manner. Preferably, the eggshell membrane is separated from the eggshell in the absence of any unwanted substance that would remain in the HA source material, e.g., the eggshell membrane. Unwanted substances can include, for example, solvents or other chemicals that remain in the HA source material, after the eggshell membrane is separated from the eggshell, which are undesirable and/or detrimental for the contemplated use of the HA isolate/composition.

Methods for separating eggshell membrane from the eggshell can include a purely mechanical manner as, for instance, by rolling and pulling the membranes away from the washed shells after removal of the yoke and albumen of fresh or uncooked eggs. Mechanical methods of separating eggshell membranes from cooked eggs are also contemplated.

A combination of mechanical and chemical means of separating the eggshell membrane from the eggshell can also be used, such as agitating coarsely chopped eggshells containing the adhering membranes in the presence of a dilute acid until the membrane separates from the shell and separating the released membranes from the shells. U.S. Pat. No. 3,194,732 to Neuhauser provides a more detailed discussion of methods for separating eggshell membrane from eggshells, which is incorporated herein by reference.

The method also preferably includes purifying the extracted hyaluronic acid composition to provide a desired HA content. The hyaluronic acid composition preferably contains at least about 80 wt %, more preferably at least about 90 wt %, and most preferably at least about 95 wt % hyaluronic acid. In one embodiment, the hyaluronic acid composition is substantially pure hyaluronic acid.

The method for isolating and/or purifying the HA composition from the eggshell membrane is generally not critical, so long as the functional characteristics of the extracted HA are not detrimentally altered for the contemplated use. Typical methods include enzymatic digestion of the HA containing source, separation to remove proteins and nucleic acids and purification to provide a crude extract. Examples of useful enzymes to carry out the enzymatic digestion include papain, chymopapain, pronase, ficin, pepsin, a yeast enzyme complex or other enzyme complexes or cocktails. Additional, purification steps typically include repeated steps of precipitation in an alcohol solution and redissolution in a NaCl solution. There are numerous examples of methods for isolating and/or purifying HA from biological sources, e.g., animal sources. Selected patent references describing methods to isolate and purify HA include U.S. Pat. Nos. 4,141,973; 4,784,990; 5,099,013; 5,166,331; 5,316,926; 5,411,874; 5,559,104 and 5,925,626.

While not being bound by theory, it is believed that the HA composition derived from eggshell membrane is free of, or at least contains a lower amount of, undesirable constituents found in other known sources of HA. For example, it is believed that HA derived from animal body tissues or fluids, or from bacterial fermentation, will typically contain certain amounts of other components which are detrimental or undesirable to an animal being administer such an HA composition. The detrimental or undesirable components can include components found in the natural source of the HA or components introduced during the processing to isolate and purify the HA, e.g., solvents. Thus, it is believed that HA derived from these known sources will contain undesirable components not found in the HA compositions derived from eggshell membrane, will contain higher levels of undesirable components or will require additional processing to obtain HA comparable to HA derived from eggshell membrane.

Accordingly, in a preferred embodiment, the HA composition derived from eggshell membrane is isolated and/or purified in the absence of any required solvent (or other material) used to process known sources of HA, which is detrimental for the contemplated use of the HA composition.

In another embodiment, the HA composition derived from eggshell membrane can be isolated and/or purified using a lower amount of solvents (or other materials) required for isolating and/or purifying HA derived from other known sources. For example, it is contemplated that HA can be extracted from the eggshell membrane using sterile water or other aqueous solutions, such as an aqueous solution containing 3% sodium acetate or a 0.05–0.15M sodium chloride solution.

In one embodiment it is contemplated that HA is extracted from eggshell membrane, in the absence of organic solvents, by initially extracting the HA using aqueous solutions. Purification can be accomplished using cetylpyridinium chloride precipitation, redissolution in sodium chloride solution and subsequent treatments using diafiltration and ultrafiltration. However, it is also contemplated in other embodiments that organic solvents will be used in one or more of the HA purification steps.

In yet another embodiment, the HA composition derived from eggshell membrane can be isolated and/or purified using fewer processing steps or less costly processing than the processing required to obtain an HA composition derived from other known sources, having the same purity as that of the HA composition derived from eggshell membrane.

The hyaluronic acid composition preferably contains a naturally occurring hyaluronic acid having an average molecular weight of less than about 1,000,000, more preferably in the range of from about 50,000 to about 500,000, and most preferably in the range from about 50,000 to about 250,000 daltons. The molecular weight can be increased by additional processing, e.g., by cross-linking the hyaluronic acid. There are numerous methods to crosslink hyaluronic acid. Selected patent references describing crosslinking methods include U.S. Pat. Nos. 4,716,224; 5,099,013; 5,783,691; and 6,030,958. In addition, selected literature references have been cited above.

In one embodiment, the hyaluronic acid composition can also include other naturally occurring materials derived from eggshell membrane. The other naturally occurring materials can include any materials found in the eggshell membrane that have medical or non-medical uses in combination with the naturally occurring HA. Preferred materials include materials selected from the group consisting of a hexosamine, chondroitin sulfate and combinations thereof, as discussed more fully above with respect to the hyaluronic acid solate.

In yet another aspect, the invention is directed to a composition for use with mammals, including both humans and animals. The composition includes hyaluronic acid derived from eggshell membrane. The composition can also include other naturally occurring constituents derived from eggshell membrane which are useful to humans or animals. These other constituents can include a hexosamine, e.g., glucosamine, and/or chondroitin sulfate.

By the Terminology "use with mammals," is intended treatment of a mammal having any condition which would benefit from the administration of HA (or administration of HA in combination with any other naturally occurring constituents from the eggshell membrane), as well as inclusion of the composition in any product intended for use by mammals. Uses of the composition can include use as an ingredient in cosmetics, nutraceuticals or pharmaceuticals. Preferred uses include use as a lubricant or moisturizing agent in cosmetics or eye drops, an orally administered nutraceutical or a locally administered composition for treatment of joints afflicted with osteoarthritis. Other uses include use as a vehicle for other pharmacological substances, in wound healing, treatment of periodontal diseases and as an osteoinductive agent. Additional uses for the isolate(s) and/or composition(s) contemplated by the present invention include all known uses for HA, such as those described more fully in U.S. Pat. No. 5,166,331 to della Valle, et al.; U.S. Pat. No. 5,559,104 to Romeo, et al.; and U.S. Pat. No. 5,646,129 to Callegaro, et al.; which are incorporated herein by reference.

Thus, in another aspect, the invention is directed to a method of treating a mammal having a condition which will benefit from the administration of HA, which includes administering a composition rich in HA derived from eggshell membrane.

In yet another aspect, the invention is directed to a method for producing a product for use with mammals which includes extracting a hyaluronic acid composition from eggshell membrane and incorporating the hyaluronic acid composition in a product for use with mammals. Preferably, the eggshell membrane is first separated from the egg white, egg yolk and eggshell prior to extracting the hyaluronic acid composition. The hyaluronic acid composition can also be purified prior to incorporation into the product for use with mammals.

Although the present invention has been described with reference to hen eggshell membrane, one skilled in the art can easily ascertain the use of eggshell membrane from other fowl including emu, ostrich, etc. Furthermore, in some examples the present application has been described with reference to a method for eggshell membrane enzyme hydrolysis and subsequent HA extraction and purification. One skilled in the art can easily ascertain various methods for eggshell membrane hydrolysis, and for extraction and purification of HA from eggshell membrane sources. Such equivalents are intended to be encompassed in the scope of the present invention. The present application also describes the analysis of eggshell membrane residue following HA extraction. This residue contains as high content of collagen, as determined by measurement of hydropxyproline. One skilled in the art can easily ascertain the use of this high collagen containing material, alone or in combination with the extracted HA, for medical and non-medical applications.

EXAMPLES

The following non-limiting examples have been carried out to illustrate preferred embodiments of the invention.

Example 1

Eggshells and attached eggshell membrane were obtained from an egg breaking facility. The eggshell membrane was first separated from eggshells. Eggshell membrane was collected and immediately packaged in plastic bags and placed in frozen storage. Samples of eggshell membrane were later retrieved for extraction and purification of HA. Samples were treated using sterile water to extract soluble HA and the extracted HA was then isolated and purified. Purified HA was then analyzed for uronic acid using the carbazole reaction. Samples of HA were also analyzed for molecular weight using HPLC techniques. Small quantities of HA were extracted of low molecular weight, between 50,000 and 100,000 daltons.

Example 2

Samples of eggshell membrane were analyzed for HA content using a very sensitive ELISA test prepared by Corgenix, Inc. This enzyme-linked binding protein assay uses a capture molecule known as hyaluronic acid binding protein (HABP) to measure HA concentration. Samples of eggshell membrane were shown to contain 5–10% HA.

Example 3

Samples of eggshell membrane were subjected to enzyme hydrolysis using a yeast enzyme complex. The hydrolysate was analyzed for uronic acid using the carbazole colorimetric assay. Hydrolysate was shown to contain between 0.1–0.3% HA. Since eggshell membrane samples were diluted approximately 1:10, HA content was between 1–3% HA.

Example 4

Samples of eggshell membrane were subjected to enzyme hydrolysis using a second enzyme cocktail composed of a yeast enzyme complex. The hydrolysate was analyzed for uronic acid using the carbazole colorimetric assay. Hydrolysate was shown to contain approximately 2% HA. Since eggshell membrane was diluted approximately 1:5, the HA content of eggshell membrane was approximately 10%.

Example 5

Wet eggshell membrane is treated with a yeast enzyme complex to reduce the eggshell membrane particles to a thick, almost clear slurry. The slurry is diafiltered using a 20,000 molecular weight cutoff membrane. NaCl is added to the retained solution to a concentration of 0.2M and the pH adjusted to 7.2 using phosphate buffer (0.2M). After pH adjustment, 1% cetylpyridinium chloride (CPC) is added to the solution at 1:60 (v/v). After mixing for 2 hours, the CPC precipitate is removed by centrifugation or filtration and ethanol added to the filtered HA solution at 2:1 (2 parts ethanol to 1 part HA solution). The precipitate is then collected by centrifugation or filtration and dissolved in 0.2M NaCl in 0.2M phosphate buffer, pH 7.2. HA is again precipitated by adding ethanol at 2:1 and the precipitate redissolved in 0.15M NaCl. The HA is again precipitated by adding ethanol at 2:1. The final precipitate is washed in acetone and air dried for storage. Additional steps may be included to purify HA for medical applications.

All references, including patents, publications, and patent applications, mentioned in this specification are herein incorporated by reference in the same extent as if each independent publication, patent or patent application was specifically and individually indicated to be incorporated by reference.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in an are within the scope of the invention as described in the appended claims.

REFERENCES

[1] Egg Science and Technology, Eds. William J. Stadelman and Owen J. Cotterill, Food Products Press, Binghamton, N.Y., 3rd edition, 1990, Pps.100–101
[2] Arias, et. al., Connective Tissue research, 36: 21–33, 1997
[3] Wu, et. al., Matrix biology, 14:507–513, 1994
[4] Carrino, et. al., Connective Tissue Research, 35: 325–329, 1996
[5] Baker, et. al., Biochem. J., 82:352, 1962
[6] Osuoji, C I, Biochim. Biophys. Acta, 244:481–483, 1971
[7] Cifonelli, J A, "The calorimetric estimation of uronic acid" In: Methodology of Connective Tissue Research, ED: DA Hall, Joynson-Bruvvers Ltd, Oxford, 1976, Chapter 26, Pp 253–256.
[8] Armstrong, D C and Johns, M R, "Improved Molecular Weight Analysis of Streptococcal Hyaluronic Acid by Size Exclusion Chromatography" in Biotechnology Techniques,
[9] J. Control Release, 69:169–184, 2000
[10] J. Biomed. Biomater, Res., 47:152–169
[11] J. Control Release, 53:93–103, 1998
[12] J. Biomed. Mater. Res., 37:243–251, 1997

We claim:

1. A method for producing a hyaluronic acid composition comprising providing eggshell membrane from a mature fowl egg and extracting a hyaluronic acid rich fraction from said eggshell membrane.

2. A method according to claim 1, wherein said eggshell membrane contains from about 0.5 to 100 wt % hyaluronic acid.

3. A method according to claim 2, wherein said eggshell membrane contains from 1 to 100 wt% hyaluronic acid.

4. A method according to claim 3, wherein said eggshell membrane contains hyaluronic acid in the range of about 1 to about 5 wt%.

5. A method according to claim 1, wherein the step of providing an eggshell membrane comprises the step of separating said eggshell membrane from the egg yolk, egg white and eggshell.

6. A method according to claim 1, wherein said hyaluronic acid composition contains at least about 80 wt % hyaluronic acid.

7. A method according to claim 6, wherein said hyaluronic acid composition contains at least about 90 wt % hyaluronic acid.

8. A method according to claim 7, wherein said hyaluronic acid composition contains at least about 95 wt % hyaluronic acid.

9. A method according to claim 8, wherein said hyaluronic acid composition is substantially pure hyaluronic acid.

10. A method according to claim 1, wherein said hyaluronic acid composition contains hyaluronic acid having an average molecular weight of less than about 1,000,000 daltons.

11. A method according to claim 10, wherein said hyaluronic acid composition contains hyaluronic acid having an average molecular weight in the range of from about 50,000 to about 500,000 daltons.

12. A method according to claim 11, wherein said hyaluronic acid has an average molecular weight in the range from about 50,000 to about 250,000 daltons.

13. A method according to claim 10, wherein the molecular weight of said hyaluronic acid is modified by increasing the average molecular weight.

14. A method according to claim 13, wherein the average molecular weight of said hyaluronic acid is increased by cross-linking the hyaluronic acid.

15. A method according to claim 1, wherein said hyaluronic acid composition comprises hyaluronic acid and at least one other naturally occurring constituent derived from eggshell membrane selected from the group consisting of a hexosamine, chondroitin sulfate and combinations thereof.

16. A method according to claim 15, wherein said hexosamine is selected from the group consisting of N-acetyl-D-glucosamine, N-acetyl-D-galactosamine, a hexose and mixtures thereof.

17. A method according to claim 15, wherein said hexosamine is present in an amount from about 0.05 to 100 wt %.

18. A method according to claim 17, wherein said hexosamine is present in the range of about 0.5 to about 10 wt %.

19. A method according to claim 18, wherein said hexosamine is present in the range of about 0.5 to about 5 wt %.

20. A method according to claim 15, wherein said chondroitin sulfate is present in an amount from about 0.05 to 100 wt %.

21. A method according to claim 20, wherein said chondroitin sulfate is present in the range of about 0.5 to about 10 wt %.

22. A method according to claim 21, wherein said chondroitin sulfate is present in an amount of at least about 0.5 to about 5 wt %.

23. A method for producing a hyaluronic acid containing product, said method comprising providing eggshell membrane from a mature fowl egg, extracting a hyaluronic acid rich fraction from said eggshell membrane and incorporating said hyaluronic acid rich fraction in a product select from the group consisting of lubricant for use in cosmetics or eye drops, a moisturizing agent for use in cosmetics or eye drops, an orally administered nutraceutical and a locally administered composition for treatment of osteoarthritis.

24. A method according to claim 23, further comprising purifying said hyaluronic acid rich fraction prior to the step of incorporating said fraction in said product.

25. A method according to claim 23, wherein said hyaluronic acid rich fraction comprises hyaluronic acid and at least one other naturally occurring constituent derived from said eggshell membrane selected from the group consisting of a hexosamine, chondroitin sulfate and combinations thereof.

26. A method according to claim 23, wherein the step of providing an eggshell membrane comprises the steps of providing mature fowl eggs having an eggshell, egg yolk, egg white and eggshell membrane, in which the eggshell encases the egg yolk, egg white and eggshell membrane, and breaching the eggshell to expose the egg yolk, egg white and eggshell membrane.

27. A method according to claim 23, wherein the step of providing an eggshell membrane comprises the steps of providing cracked eggs having an eggshell and an eggshell membrane attached to the eggshell, and separating the eggshell membrane from the eggshell.

28. A method according to claim 1, wherein the step of providing an eggshell membrane comprises the steps of providing mature fowl eggs having an eggshell, egg yolk, egg white and eggshell membrane, in which the eggshell encases the egg yolk, egg white and eggshell membrane, and breaching the eggshell to expose the egg yolk, egg white and eggshell membrane.

29. A method according to claim 1, wherein the step of providing an eggshell membrane comprises the steps of providing cracked eggs having an eggshell and an eggshell membrane attached to the eggshell, and separating the eggshell membrane from the eggshell.

* * * * *